United States Patent
Daniel et al.

(10) Patent No.: US 8,728,100 B2
(45) Date of Patent: May 20, 2014

(54) SUTURING ASSEMBLY PROVIDING BI-DIRECTIONAL NEEDLE MOVEMENT THROUGH UNI-DIRECTIONAL ACTUATOR MOVEMENT

(75) Inventors: Geoffrey A. Daniel, Crystal, MN (US); Allen Gaynor, Coon Rapids, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/523,909

(22) Filed: Jun. 15, 2012

(65) Prior Publication Data

US 2012/0323261 A1 Dec. 20, 2012

Related U.S. Application Data

(60) Provisional application No. 61/499,698, filed on Jun. 22, 2011.

(30) Foreign Application Priority Data

Jun. 17, 2011 (DK) ................................. 2011 70308

(51) Int. Cl.
*A61B 17/062* (2006.01)
(52) U.S. Cl.
USPC ........................................................ 606/144
(58) Field of Classification Search
USPC ........................... 606/144–147, 139; 112/169
See application file for complete search history.

(56) References Cited

U.S. PATENT DOCUMENTS

| | | | |
|---|---|---|---|
| 6,923,819 B2 * | 8/2005 | Meade et al. | 606/144 |
| 2008/0132919 A1 * | 6/2008 | Chui et al. | 606/145 |
| 2010/0094083 A1 * | 4/2010 | Taylor et al. | 600/106 |
| 2011/0022063 A1 * | 1/2011 | McClurg et al. | 606/145 |
| 2011/0046644 A1 * | 2/2011 | McClurg et al. | 606/144 |
| 2011/0092985 A1 * | 4/2011 | Gaynor et al. | 606/139 |
| 2011/0092991 A1 * | 4/2011 | Gaynor et al. | 606/148 |
| 2011/0224697 A1 * | 9/2011 | Deitch et al. | 606/144 |
| 2011/0224698 A1 * | 9/2011 | Deitch et al. | 606/144 |
| 2012/0143222 A1 * | 6/2012 | Dravis et al. | 606/145 |
| 2012/0172897 A1 * | 7/2012 | McClurg et al. | 606/144 |
| 2012/0197270 A1 * | 8/2012 | McClurg | 606/144 |
| 2012/0209298 A1 * | 8/2012 | McClurg et al. | 606/144 |
| 2012/0221022 A1 * | 8/2012 | Devens et al. | 606/144 |
| 2013/0023905 A1 * | 1/2013 | Kubalak | 606/144 |
| 2013/0023906 A1 * | 1/2013 | Kubalak | 606/144 |

FOREIGN PATENT DOCUMENTS

| | | |
|---|---|---|
| EP | 0669102 | 8/1995 |
| EP | 1813198 | 8/2007 |

* cited by examiner

*Primary Examiner* — Julian W Woo
*Assistant Examiner* — Shaun L David
(74) *Attorney, Agent, or Firm* — Coloplast Corp., Coloplast A/S; NIck Baumann

(57) ABSTRACT

A suturing assembly includes shaft attached between a handle and a head. The handle includes a brace and an actuator attached to the handle, where the actuator has a neutral position that is distal the brace. The shaft defines a longitudinal axis of the assembly. The head includes a proximal portion housing a needle that is movable through a needle exit port, and a distal end spaced apart from the proximal portion by a throat. The distal end is radially offset from the longitudinal axis and defines a cavity. Movement of the actuator from the neutral position to the brace moves the needle both in a first direction out of the needle exit port into the cavity and in a second direction out of the cavity and into the needle exit port.

8 Claims, 11 Drawing Sheets

SUTURING ASSEMBLY PROVIDING BI-DIRECTIONAL NEEDLE MOVEMENT THROUGH UNI-DIRECTIONAL ACTUATOR MOVEMENT

BACKGROUND

Intracorporeal suturing of tissue during surgery presents challenges to the surgeon in that the surgeon is called upon to manipulate suturing instruments within the confines of a relatively small incision formed in the patient's body. In some cases, the surgeon digitally palpates a desired location for placement of the suture and is unable to see the suture site.

Improved suturing instruments and improved methods of delivering sutures would be welcomed by the surgical staff.

SUMMARY

One aspect provides a suturing assembly configured to place suture in tissue. The suturing assembly includes a shaft attached between a handle and a head. The handle includes a brace and an actuator attached to the handle, where the actuator has a neutral position that is distal the brace. The shaft is coupled to the handle and defines a longitudinal axis of the assembly. The head is coupled to the shaft and includes a proximal portion housing a needle that is movable through a needle exit port, and a distal end spaced apart from the proximal portion by a throat. The distal end of the head is radially offset from the longitudinal axis and defines a cavity. Movement of the actuator from the neutral position to the brace moves the needle both in a first direction out of the needle exit port into the cavity formed in the distal end of the head and in a second direction out of the cavity formed in the distal end of the head and into the needle exit port.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
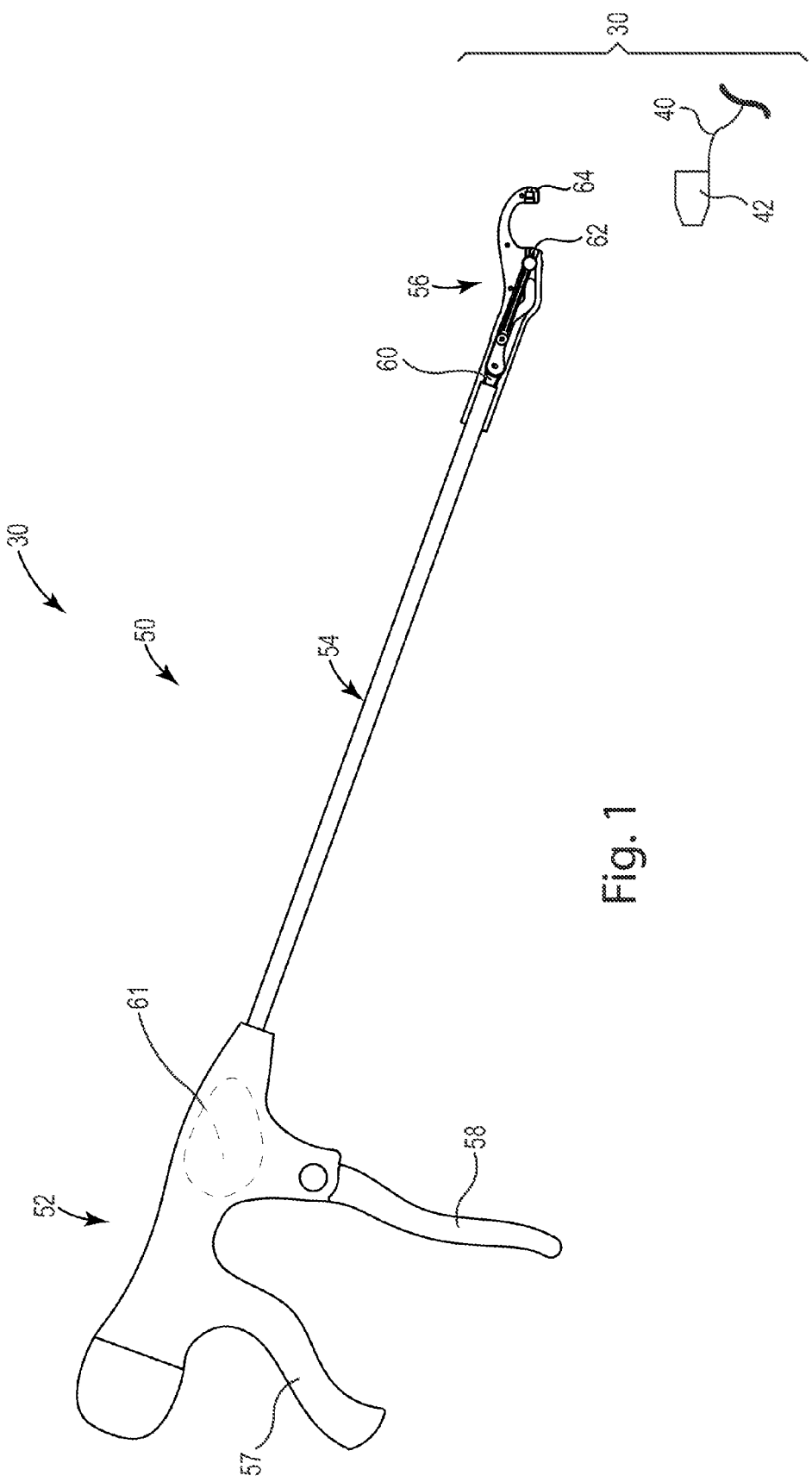
FIG. 1 is a side view of one embodiment of a suturing system that includes a suturing assembly, a suture, and a capsule attached to the suture.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

In this specification, shunt means to move an object away from a first axis to another axis that is different from the first axis. For example, in one embodiment a suturing device includes a needle that is moved in a first direction (e.g., along a longitudinal axis) and is subsequently moved in a second direction different from the first direction (i.e., away from the longitudinal axis); thus the needle is shunted away from a longitudinal axis when deployed from the device.

In this specification, end means endmost and end portion means that segment that is adjacent to and extends from the end. For example, a proximal end is that end location of a handheld instrument that is nearest a user, and a proximal end portion is that segment (e.g., a handle of the handheld instrument) that is adjacent to and extends distally away from the proximal end.

Embodiments provide a suturing assembly having a shaft attached between a handle and a head. The handle includes a thumb/palm brace and an actuator attached to the handle, where the actuator has a neutral position that is distal the thumb/palm brace. The head is coupled to the shaft and includes a proximal portion housing a needle that is movable through a needle exit port, and a distal end spaced apart from the proximal portion by a throat. Movement of the actuator from the neutral position to the thumb/palm brace moves the needle both in a first direction out of the needle exit port and in a second direction out of the cavity formed in the distal end of the head and into the needle exit port. In this manner, uni-directional movement of the actuator provides bi-directional needle movement first out of and then back into the needle exit port. Thus, squeezing the actuator one time to the handle provides the user with confidence that the full range of needle movement of the needle has been achieved.

In one embodiment, the suture assembly includes a capsule that is attached to a length of suture. The capsule is sized for retention within the cavity formed in the head. The uni-directional movement of the actuator provides bi-directional needle movement out of the needle exit port and into the cavity where the needle engages with the capsule, and out of the cavity and back to the needle exit port where the needle delivers and disengages from the capsule. Thus, squeezing the actuator to the handle provides the user with confidence that the capsule has been engaged and delivered to the needle exit port.

FIG. 1 is a side view of one embodiment of a suturing system 30 useful for placing suture in tissue. The suturing system 30 includes a suture 40 attached to a capsule 42 and a suturing assembly 50 that is provided to form a channel in tissue to subsequently draw the capsule 42 and the suture 40 through the channel formed in the tissue to throw a suture stitch.

The suture 40 is selected from acceptable surgical suture materials and is attached mechanically, chemically, or adhesively to the capsule 42, both components of which are described below in FIG. 4.

The suturing assembly 50 includes a handle 52, a shaft 54 coupled to the handle 52, and a head 56 coupled to the shaft 54. The handle 52 thus defines a proximal end of the suturing assembly 50 and is nearest a user of the suturing assembly 50.

In one embodiment, the handle 52 includes a thumb/palm brace 57 and an actuator 58 that is attached to the handle distal of (or forward of) the thumb/palm brace 57. The actuator 58 communicates with a rod 60 that is disposed within the shaft 54, and the rod 60 communicates with a needle 62 that is retained in the head 56. The capsule 42 is removably retained in a cavity formed in a distal end 64 of the head 56 and when so positioned is adapted for engagement with the needle 62.

Figure 2A:
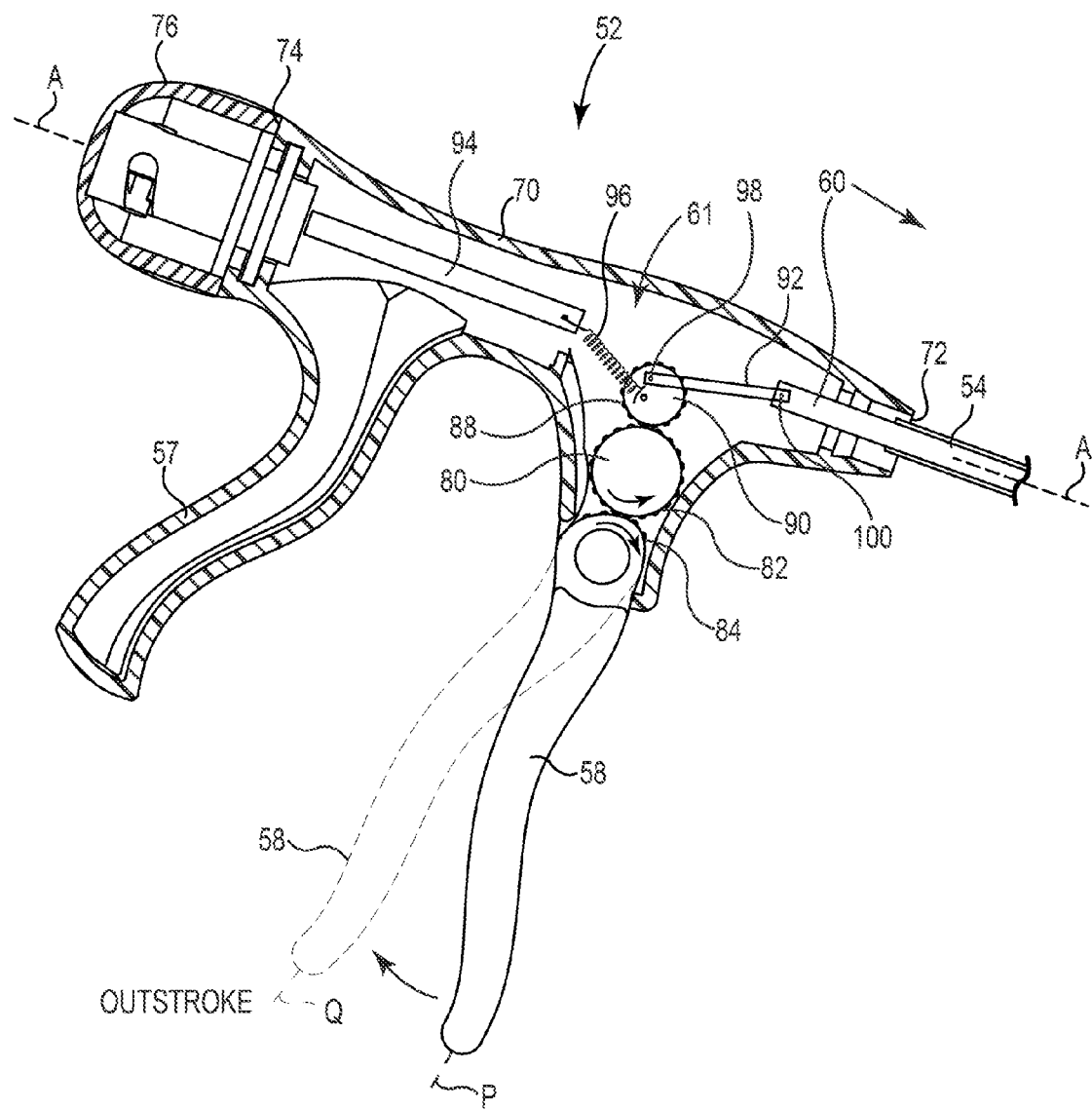
FIG. 2A is a schematic view of one embodiment of components of a handle of the suturing assembly illustrated in FIG. 1 with an actuator of the handle moving from a neutral position to a second position.
Figure 2B:
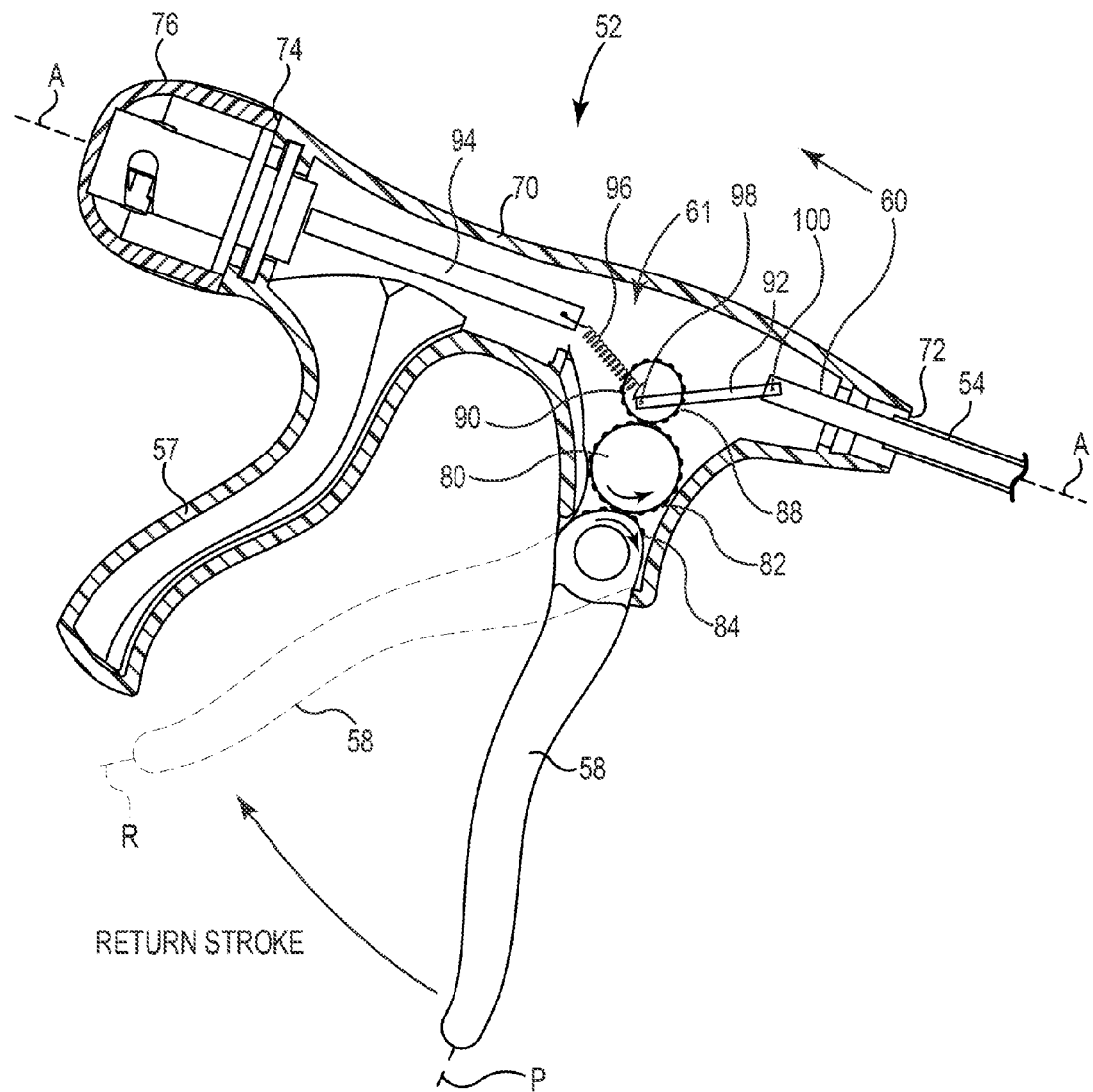
FIG. 2B is a schematic view of the actuator of the handle in a third and fully activated position.
Figure 2C:
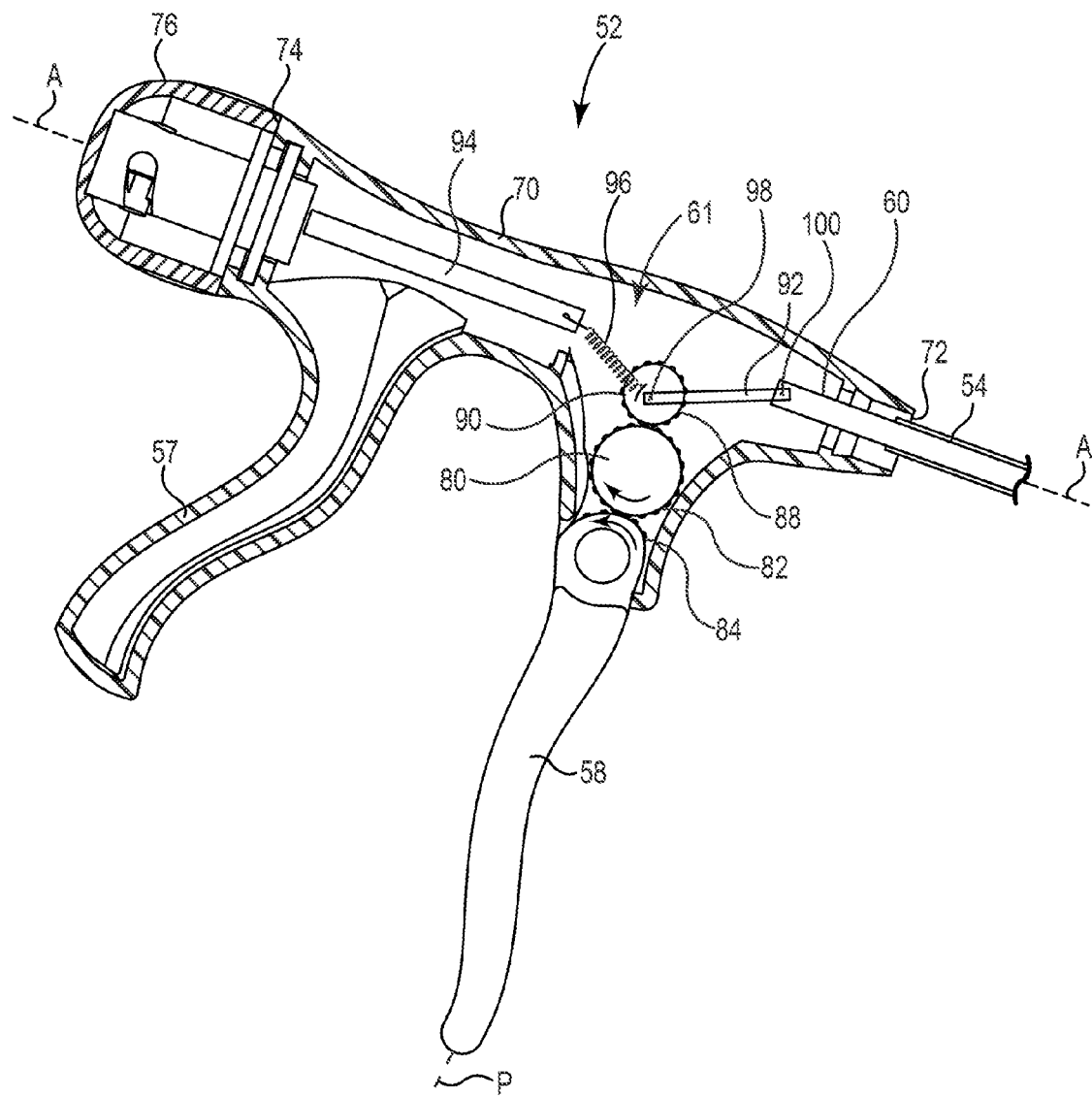
FIG. 2C is a schematic view of the actuator of the handle returned to the neutral position.

In one embodiment, a mechanism 61 described below in FIGS. 2A-2C is housed inside of the handle 52 and is configured to translate a uni-directional movement of the actuator 58 into a bi-directional movement (distal/forward movement followed by proximal/rearward movement) of the needle 62. For example, a single squeeze of the actuator 58 from its at-rest neutral position to the thumb/palm brace 57 moves the needle 62 in a distal direction out of an initial parked location inside of the head 56 to the distal end 64 of the head 56 and back again to the initial parked location inside of the head 56. In particular, the uni-directional movement of the actuator 58 moves the needle 62 in a first direction out of the initial parked location inside of the head 56 to the capsule 42 in the distal end 64 of suturing assembly 50, at which location the needle 62 engages with the capsule 42, and the mechanism 61 operates to retrieve the needle 62 and the capsule 42 from the distal end 64 of suturing assembly 50 back into the initial parked location inside of the head 56. Thus, the uni-directional movement of the actuator 58 causes the needle to move out and back from its initial parked position, and further operates to capture the capsule 42 when the needle 62 is in the extended out position.

Suturing assembly 50 is suited for the intracorporeal suturing of tissue during surgery, and in one embodiment is provided as a sterile, disposable surgical instrument that is discarded after the surgical procedure. To this end, the components of assembly 50 are selected to be compatible with gas, steam, or radiation sterilization.

FIGS. 2A-2C illustrate embodiments of the mechanism 61 housed within the handle 52 that is provided to translate the uni-directional movement of the actuator 58 into bi-directional movement of the needle 62.

In one embodiment, the handle 52 includes a body 70 extending between a distal end 72 and a proximal end 74 with a knob 76 coupled to the proximal end 74. A major longitudinal axis A of the assembly 50 is defined that extends between the distal end 72 and the proximal end 74 of the handle 52. The thumb/palm brace 57 and the actuator 58 extend laterally (e.g., radially) away from the major longitudinal axis A of the body 70. In one embodiment, the knob 76 rotates relative to the proximal end 74 of the handle 52 to disengage the needle 62 from the capsule 42 after a stitch is thrown. The shaft 54 is coupled to the distal end 72 of the body 70, and the rod 60 is disposed within the shaft 54 and coupled between the actuator 58/mechanism 61 and the needle 62.

One suitable embodiment of the shaft 54 includes a substantially rigid aluminum annular tube extending between a proximal end that is attachable to the handle 52 and a distal end that is attachable to the head 56 (FIG. 1). Other substantially rigid materials, such as stainless steel, are also suitable selections for fabricating the shaft 54. Another embodiment of the shaft 54 includes a distal end portion that is flexible and configured to bend laterally to enable the surgeon to selectively direct the head 56 to a desired location.

The body 70 is suitably fabricated from metal or plastic, for example injection molded plastic. Suitable plastic materials for the fabrication of the body 70, the brace 57, and the knob 76 include, as examples, polycarbonate, polyethylene, acrylonitrile butadiene styrene, acrylic, or nylon. In one embodiment, the brace 57 is integrally molded with a clamshell-style of body 70 and these two components are joined together to retain the actuator 58 and the knob 76. The actuator 58 is formed to have sufficient strength to resist bending when activated by the human hand. Suitable materials for forming the actuator 58 include metal such as aluminum or plastics such as polyetherimide or poly-ether-ether-ketone.

FIG. 2A illustrates movement of the actuator 58 of the mechanism 61 to move the needle 62 in an outward/distal direction for engagement with the capsule 42 and the suture 40 (FIG. 1). In one embodiment, the mechanism 61 includes a transfer gear 80 having a surface 82 that interacts between a surface 84 of the actuator 58 and a surface 88 of a wheel 90. The wheel 90 is attached to the rod 60 by a link 92 and is attached to a retractor 94 by a spring 96. In one embodiment, the link 92 is connected to the wheel 90 at a pivot point 98 and is attached to the rod 60 at a separate pivot point 100.

In one embodiment, the surface 82 of the transfer gear 80, the surface 84 of the actuator 58, and the surface 88 of the wheel 90 are geared surfaces that move in a gear-train relationship as the actuator 58 is moved. In one embodiment, the surface 82 of the transfer gear 80, the surface 84 of the actuator 58, and the surface 88 of the wheel 90 are friction interface surfaces that move in a frictional unison as the actuator 58 is moved. In any regard, the mechanism 61 is configured to translate uni-directional movement of the actuator 58 into a more forceful bi-directional movement of the rod 60 (and therefore the needle 62).

In one embodiment, the diameter of the wheel 90 is smaller than the diameter of the transfer gear 80. In this manner, relatively small movements or rotation of the transfer gear 80 translate into relatively large movements or rotation of the surface 88 of the wheel 90, and the movement of the wheel 90 drives movement of the rod 60 and the needle 62.

FIG. 2A illustrates the actuator 58 moving from a neutral position P to a second position Q. The neutral position P is defined to be the at-rest position of the actuator 58, which is the position that the actuator 58 is in when the assembly is not in use. Moving the actuator 58 from the neutral position P to the second position Q causes the surface 84 to rotate in a clockwise sense, which causes the surface 82 to rotate in a counter-clockwise sense. When the surface 82 of the transfer gear 80 rotates in the counter-clockwise sense, the surface 88 of the wheel 90 rotates in a clockwise sense such that the link 92 is displaced or translated in a distal direction, which translates or displaces the rod 60 in a distal direction to drive the needle 62 (FIG. 1) out of the head 56.

FIG. 2B illustrates the actuator 58 moving from the neutral position P past the second position Q (FIG. 2A) to a third and fully activated position R. Movement of the actuator 58 to the third position R results in the rod 60 (and thus the needle 62) being retracted away from the distal end 64 of the head 56 (identified as a return stroke). In particular, movement of the actuator 58 from the neutral position P to the third position R further rotates the surface 84 of the actuator 58 in a clockwise sense, which through operation of the mechanism 61 as described above causes the wheel 90 to rotate an additional amount in a clockwise sense. As illustrated in FIG. 2B, the additional clockwise rotation of the wheel 90 draws the link 92 upwards and backwards in the proximal direction toward the retractor 94, which results in the rod 60 and needle 62 being retracted away from the distal end 64 of the head 56. Thus, the uni-directional movement of the actuator from the neutral position P to the third position R causes the needle 62 to move in a distal direction for engagement with the capsule 42 and then back again in a proximal direction to deliver the capsule 42 into a parked position within the head 56.

FIG. 2C illustrates the actuator 58 returned from the third position Q back to the neutral position P. When actuator 58 is in the neutral position P the mechanism 61 is reloaded to drive subsequent bi-directional movement of the needle 62. For example, in one embodiment, after movement of the actuator 58 to the third position Q, the retractor 94 and the spring 96 cooperate to bias the wheel 90 back to a neutral position to reload the mechanism 61 for subsequent bi-directional movement in response to uni-directional movement of the actuator 58.

Figure 3:
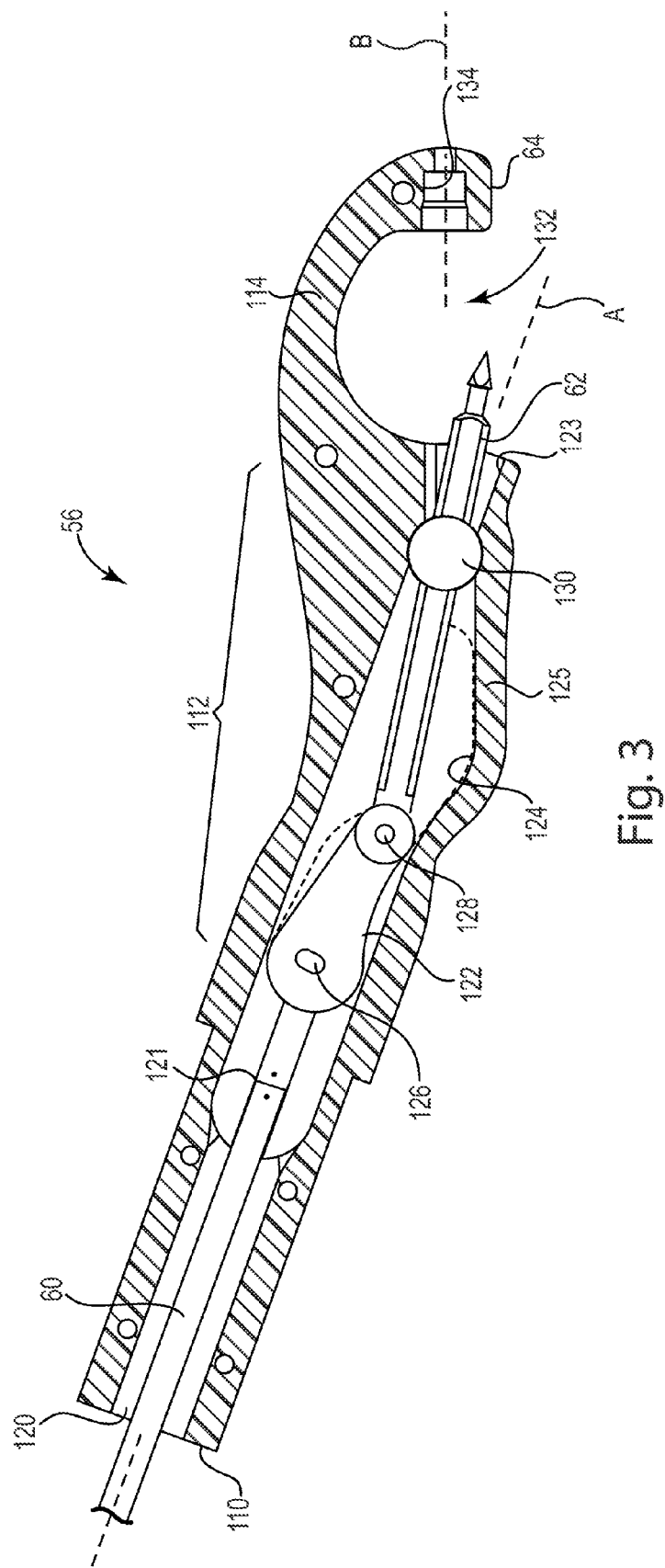
FIG. 3 is a side view of one embodiment of a head of the suturing assembly illustrated in FIG. 1.

FIG. 3 is a cross-sectional view of the head 56 showing the needle 62 protruding out of a needle exit port 123 for ease of illustration. It is to be understood that the needle 62 is parked in the needle exit port 123 when the actuator 58 is in the neutral position P (FIG. 2A) and the needle 62 extends into the cavity 134 when the actuator 58 is in the third position Q (FIG. 2B).

In one embodiment, the head 56 is formed of two mating clamshell components, and the view of FIG. 3 is taken with one-half of the clamshell structure removed so that the internal features of the mechanism 61 are visible. The head 56 is molded from plastic, for example from a polyetherimide plastic sold under the trademark Ultem, or from glass-filled polyetherimide plastics also sold under the trademark Ultem.

In one embodiment, the head 56 includes a proximal end 110 opposite the distal end 64, a proximal end portion 112 extending from proximal end 110, and a neck 114 that extends between the proximal end portion 112 and the distal end 64. The head 56 is attachable to the shaft 54, and in one embodiment includes an opening 120 sized to receive the shaft 54 such that the rod 60 extends into the proximal end portion 112 and couples with a link 122 that is attached to needle 62. In one embodiment, the distal end 64 is aligned with an axis B that is offset radially from the longitudinal axis A. Offsetting the distal end 64 from the longitudinal axis A more comfortably positions the shaft 54 for manipulation by the surgeon as the head 56 is engaged with tissue of the pelvic cavity.

In one embodiment, a clevis pin 121 connects a proximal end of the link 122 to the rod 60 and a distal end of the link 122 is coupled to the needle 62. Movement of the rod 60 by the mechanism 61 moves the link 122, which moves the needle 62 into and out of the needle exit port 123 formed in the proximal end portion 112. In one embodiment, a trace 124 is formed on an interior surface 125 of the proximal end portion 112 of the head 56, and the link 122 is configured to translate and rotate within the trace 124 to translate the needle 62 along the axis A and pitch the needle 62 up/down relative to the axis A. For example, in one embodiment the link 122 includes a first pin 126 that couples with the clevis 121 and a second pin 128 that couples with the needle 62. Axial movement of the rod 60 by the mechanism 61 translates to axial movement of the link 122 and the needle 62, and the link 122 rotates about the pins 126, 128 to shunt a path of the needle 62 off of the axis A.

The link 122 is thus configured to translate within the trace 124 to move the needle 62 in/out relative to the needle exit port 123, and rotate relative to the pins 126, 128 to direct movement of the needle 62 up/down relative to the longitudinal axis A. In one embodiment, the proximal end portion 112 includes a guide pin 130 that defines a bore sized to receive the needle 62. The needle 62 is configured to slide through the bore formed in the guide pin 130, and the guide pin 130 is rotatable to allow the needle 62 to pitch relative to the longitudinal axis A as the needle 62 moves axially, for example as the needle 62 moves into engagement with the distal end 64.

The neck 114 extends between the proximal end portion 112 and the distal end 64 and defines a throat 132. The needle 62 is movable from the proximal end portion 112, out of the needle exit port 123, across the throat 132, and into the cavity 134 formed in distal end 64. In one embodiment, the distal end 64 and the cavity 134 are both radially spaced away from the longitudinal axis A, and the guide pin 130 rotates to enable the needle 62 to move out of the needle exit port 123, pitch upwards, and into the cavity 134. In one embodiment, a top surface of the neck 114 defines an open, exposed groove (not shown) that is configured to receive and guide the suture 40 that is attached to the capsule 42 (FIG. 1).

Figure 4:
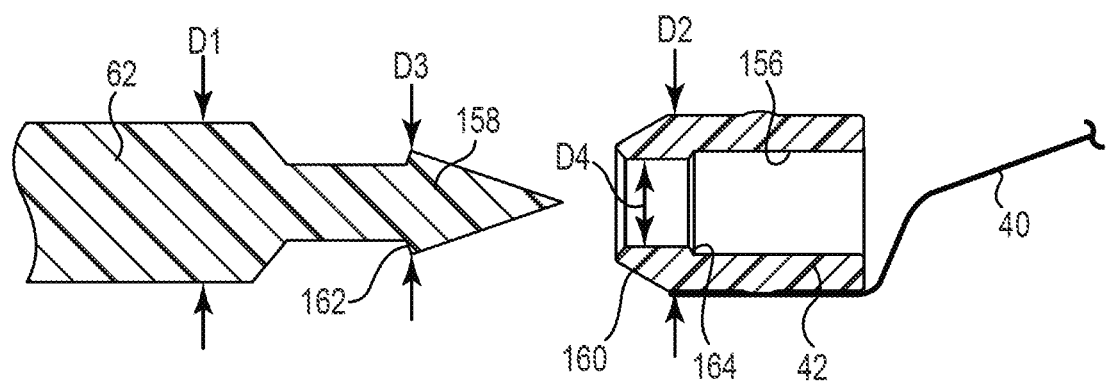
FIG. 4 is a cross-sectional view of the suture attached to the capsule as illustrated in FIG. 1 and configured to couple with a needle of the suturing assembly.

FIG. 4 is a side view of the needle 62 aligned for engagement with the capsule 42 that is attached to the suture 40. The needle 62 is preferably machined from metal such as stainless steel or a shape memory alloy such as NITINOL (Nickel Titanium Naval Ordinance Laboratory), as examples. In one embodiment, the capsule 42 is molded from plastic and formed integrally around an end of the suture 40. Suitable plastic materials for fabricating capsule 42 include polypropylene, polysulfone, urethane, or polyetherimide as examples. Suture 40 includes monofilament suture, braided suture, coated suture materials or the like, as examples.

In one embodiment, the needle 62 is shaped to promote secure engagement with the capsule 42 and a leading end 158 is formed to have a conical point with a shoulder 162 that is sized to be pressed into engagement with a flange 164 of a recess 156. For example, the flange 164 is shaped and sized to frictionally engage (e.g., snap-fit) in a "locked" manner with a shoulder 162 of the needle 62 as the needle 62 is driven into the recess 156. The capsule 42 is detachable from the needle 62 when the capsule 42 is parked in the needle exit port 123 (FIG. 3).

The conical point of the needle 62 is configured to form a channel when advanced through tissue, and the capsule 42 is sized to be pulled through the channel in the tissue made by the needle 62. In one embodiment, the leading end 160 of the capsule 42 is chamfered and the needle 62 is configured to draw the chamfered (or truncated) end 160 of the capsule 42 first through the tissue. In one embodiment, the leading end 160 of the capsule 42 is a blunt end similar to that illustrated for the trailing end of the capsule 42, and the needle 62 is configured to draw the blunt end of capsule 42 blunt end-first through the tissue.

In one embodiment, the needle 62 has a first diameter D1 and the capsule 42 has a diameter D2, where the diameter D1 is equal to or greater than the diameter D2. In this manner, the capsule 42 is sized to follow the needle 62 and be retracted through the channel formed in the tissue by the needle 62.

The leading end 158 of the needle 62 is sized to frictionally engage with the recess 156 formed in the capsule 42. For example, in one embodiment the leading end 158 has a diameter D3 that is slightly greater than a diameter D4 formed in an opening of the recess 156. In this manner, when the leading end 158 of the needle 62 is inserted into the recess 156, the leading end 158 is forced into and seats within and captures the capsule 42.

Figure 5A:
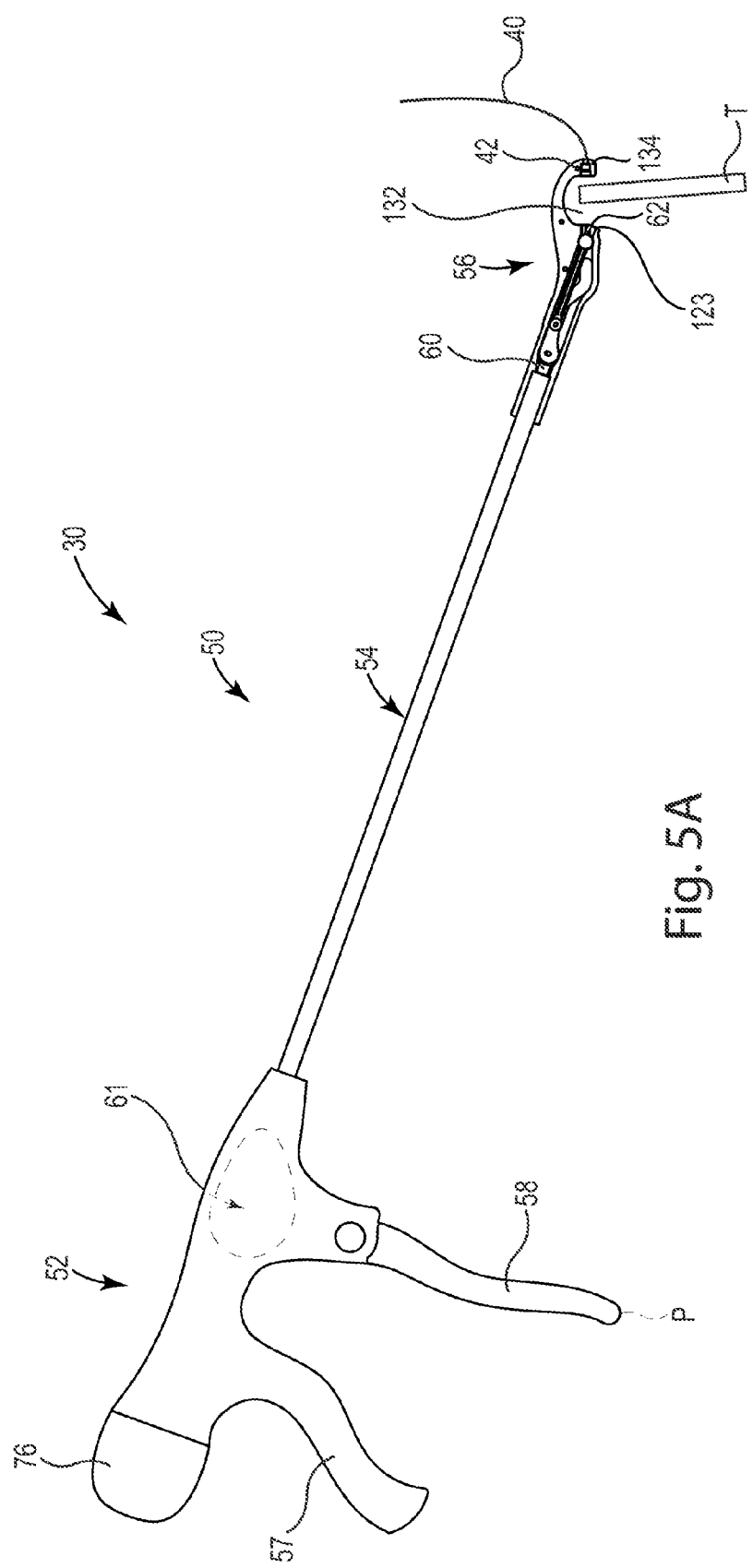
FIGS. 5A-5C are side views of one embodiment of the system placing the suture through tissue.
Figure 5B:
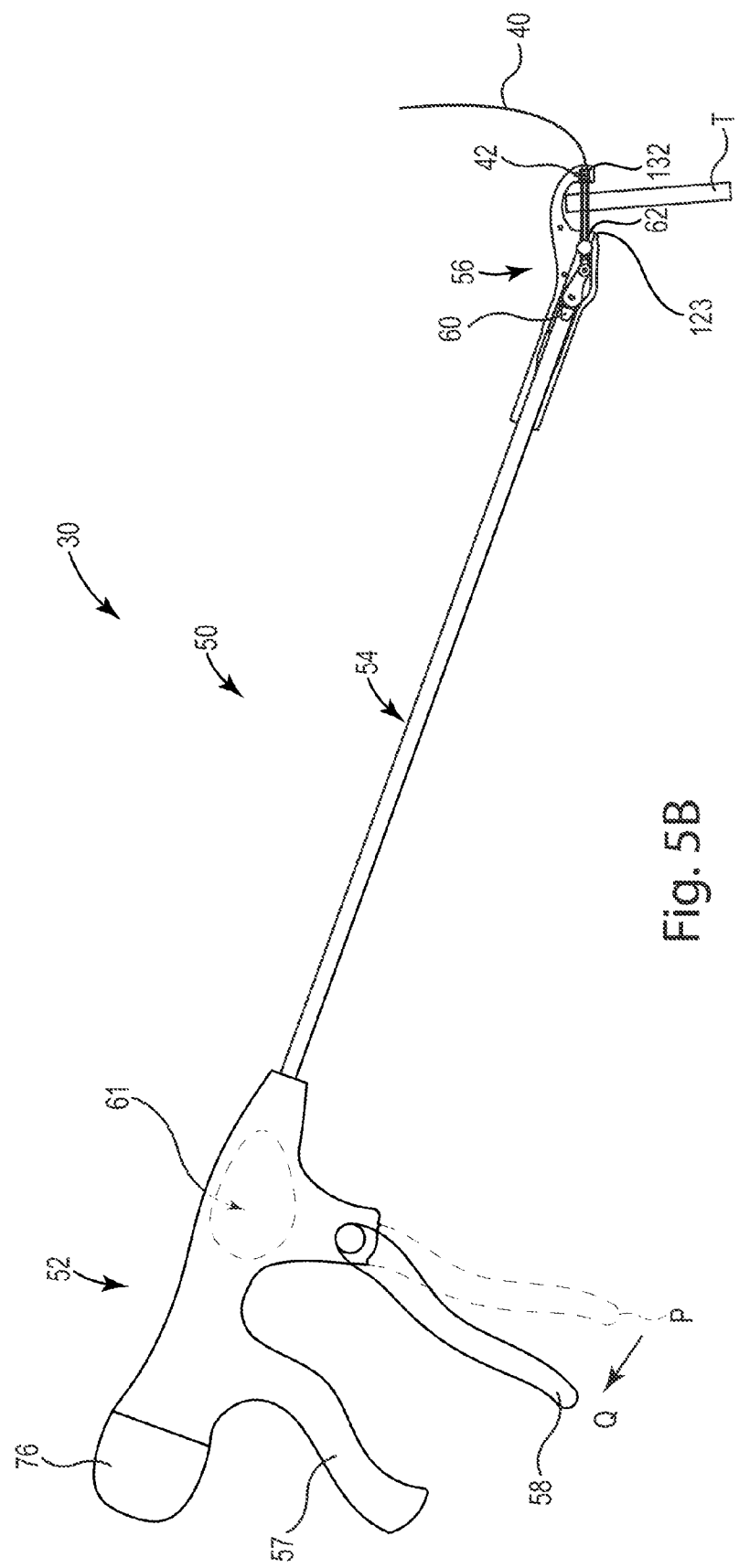
Figure 5C:
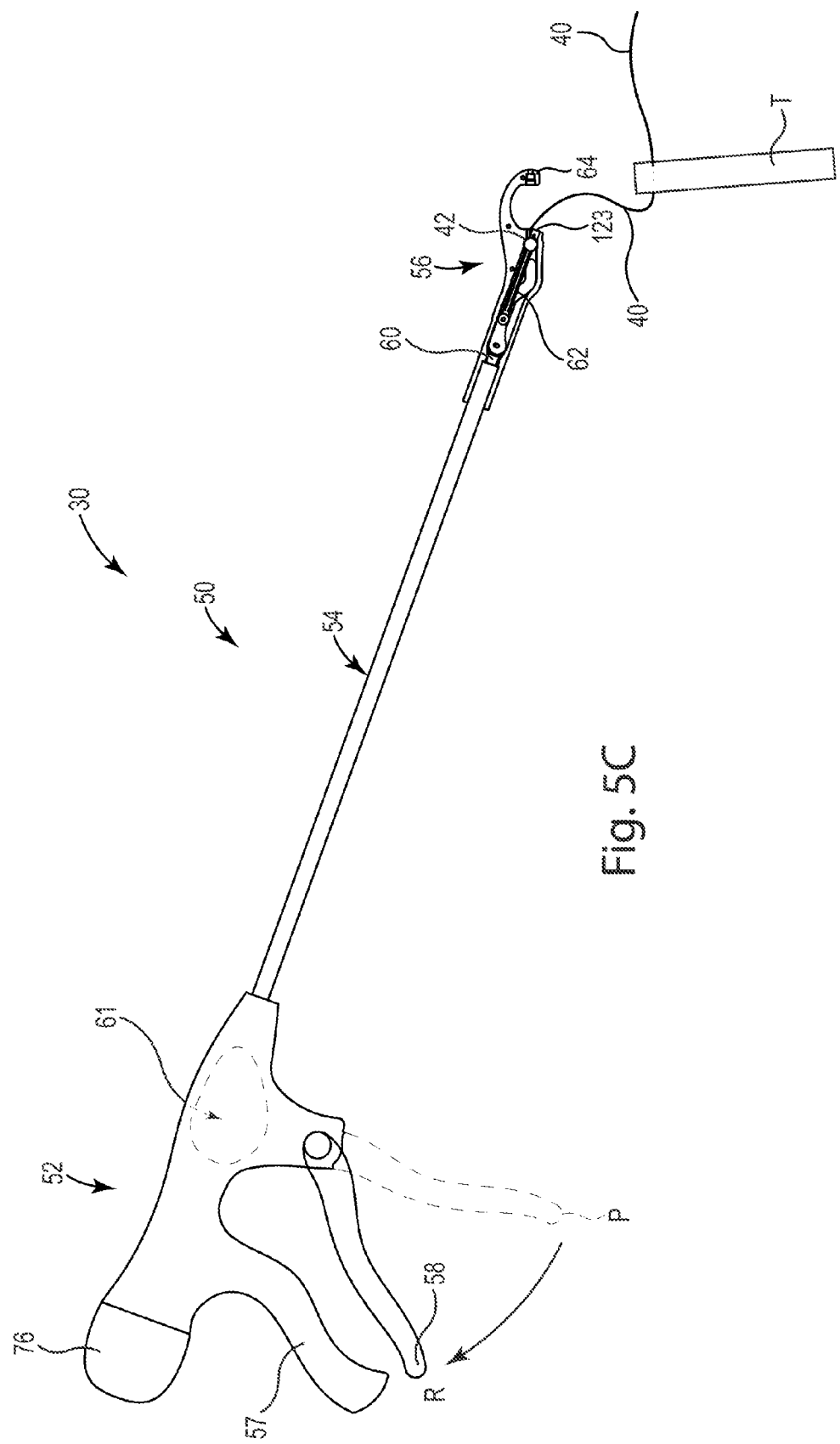

FIGS. 5A-5C are side views of the system 30 positioned to place the suture 40 through tissue T. The tissue T includes tissue in the pelvic cavity or any soft tissue, such as connective tissues such as ligaments and tendons, or other tissue such as muscle. Operation of the suturing assembly 50 includes placing the throat 132 over a target tissue T, directing the needle 62 through the tissue T to form a channel in the tissue T, engaging the needle 62 with the capsule 42 retained in the cavity 134, and drawing the needle 62 and the capsule 42 through the tissue T to place the suture 40 through the tissue T.

FIG. 5A is a side view of the system 30 with the head 56 positioned such that the throat 132 is engaged with the tissue T. The actuator 58 is in the neutral position P and the needle 62 is parked in the needle exit port 123.

FIG. 5B is a side view of the system 30 with the actuator 58 moved to the second position Q. In the second position Q the needle 62 has been advanced from the needle exit port 123 through the tissue T and engaged with the capsule 42. The needle 62 forms a channel in the tissue T as it passes through the tissue T.

FIG. 5C is a side view of the system 30 with the actuator 58 moved to the third position R in which the needle 62 and the capsule 42 are retracted into the needle exit port 123. The suture 40 is connected to the capsule 42 and is pulled through the channel that is formed in the tissue T after the needle 62 and the capsule 42 have moved in the proximal direction through the tissue T back to the needle exit port 123. The suturing assembly 50 is removed away from the tissue T leaving the suture 40 extending through the tissue T. In a gynecological procedure, the surgeon removes the suturing assembly 50 from the patient's body but still has access to the target tissue T since the suture 40 trails through the incision back to the target tissue T. In an exemplary embodiment, the incision is a single vaginal incision and the target tissue is a pelvic ligament such that surgeon has access to the ligament as provided by the suture 40 that trails away from the ligament through the vaginal incision.

Embodiments of the system 30 provide a suturing assembly 50 that translates uni-directional movement of an actuator into bi-directional movement of a suturing needle. The uni-directional movement of the actuator from the neutral position P to the third position R in which the actuator is adjacent to the thumb/palm brace 57 accomplishes a full range of suturing motion of the needle first in a distal direction to capture the suture and that in a proximal direction to pull the suture through the tissue.

Figure 6:
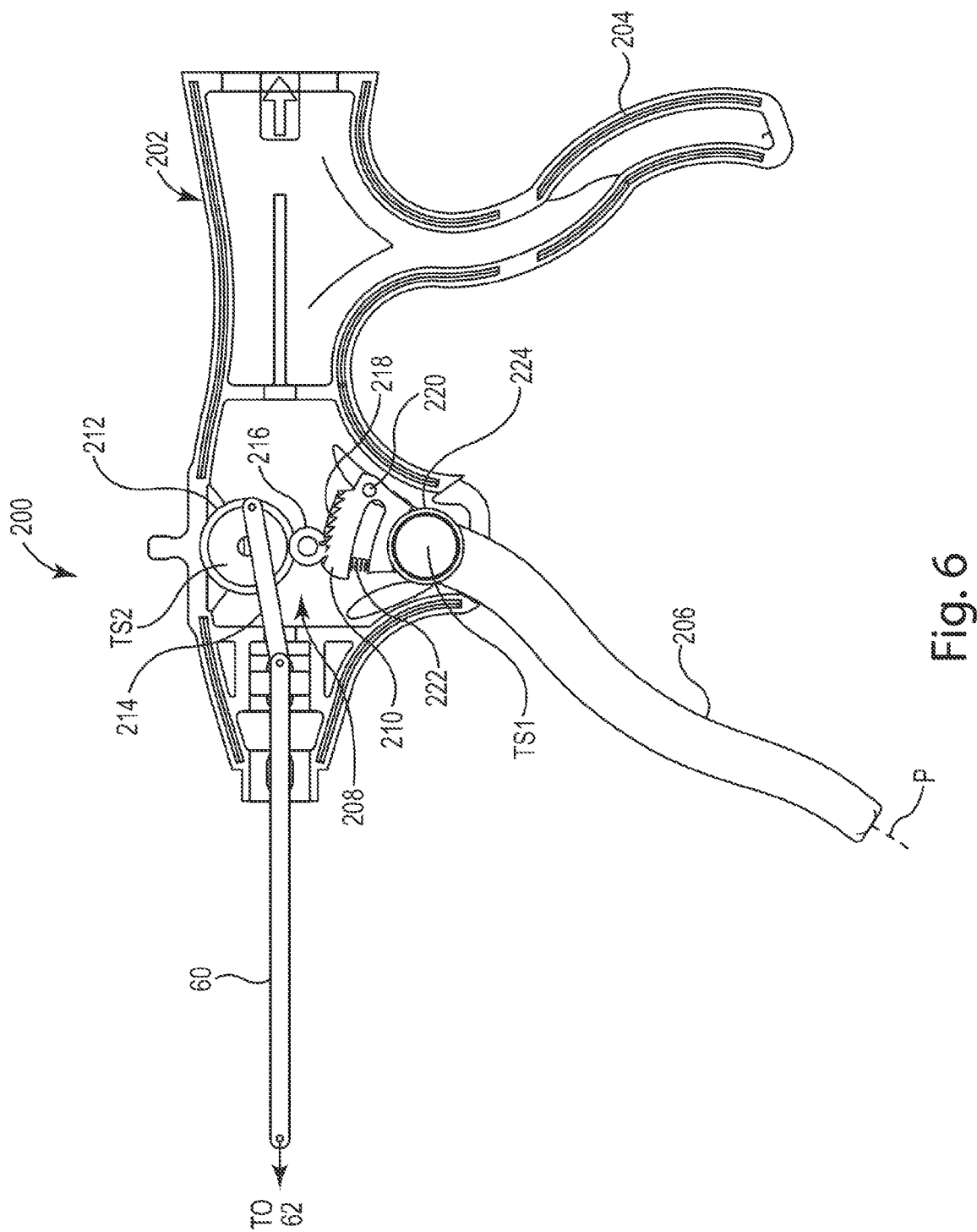
FIG. 6 is a schematic view of one embodiment of components of a handle of a suturing assembly.

FIG. 6 is a side schematic view of one embodiment a handle 202 of a suturing assembly 200. A portion of the housing of the handle 202 is removed for visual clarity of the internal components. The handle 202 includes a thumb/palm brace 204 and an actuator 206 attached to the handle 202. The actuator 206 has a neutral position P illustrated in FIG. 6 that is distal to the thumb/palm brace 204. Although not shown entirely in FIG. 6, embodiments of the suturing assembly 200 include the rod 60 that connects between the needle 62 and the actuator 206. With concurrent reference to FIG. 3, in one embodiment movement of the actuator 206 from the illustrated neutral position toward the thumb/palm brace 204 activates a mechanism 208 inside of the handle 202 that moves the needle 62 both in a first direction out of the needle exit port 123 into the cavity 134 formed in the distal end 64 of the head 56 and in a second direction out of the cavity 134 formed in the distal end 64 of the head 56 and into the needle exit port 123.

In one embodiment, the mechanism 208 includes a rack 210 attached to the actuator 206, a drive wheel 212 attached to the rod 60 by a link 214, and a transfer gear 216 that engages between the rack 210 and a drive wheel 212.

In one embodiment, the rack 210 has an engagement surface 218 and is attached to the actuator 206 by a pivot pin 220 and a compression spring 222. The compression spring 222 ensures that the rack 210 is engaged with the transfer gear 216 during an outward stroke of the rod 60. In one embodiment, the mechanism 208 includes a torsion spring TS1 that is maintained within a hub 224 attached to the actuator 206. The torsion spring TS1 operates to return the actuator 206 to the neutral position P after completion of the outward stroke of the rod 60.

In one embodiment, a separate torsion spring TS2 is maintained inside of the drive wheel 212 and operates to return the drive wheel 212 and the link 214 to the neutral position P after completing a full outward and return stroke of the needle 62, as described below.

Figure 7:
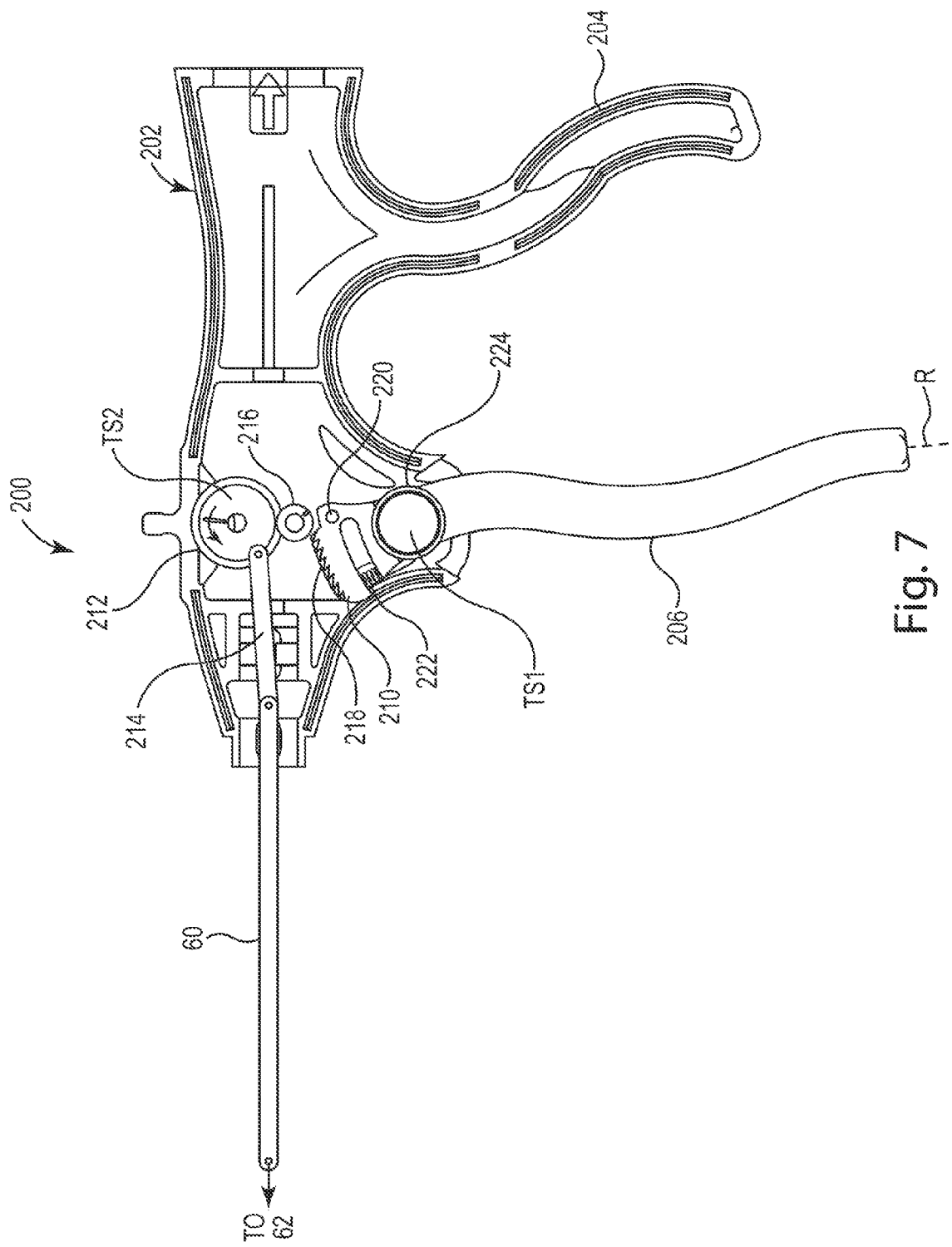
FIG. 7 is a schematic view of one embodiment of components of a handle of a suturing assembly.

FIG. 7 is a side schematic view of one embodiment the handle 202 with the actuator 206 adjacent to the thumb/palm brace 204 in a fully activated position R. In the fully activated position R the rod 60 has moved in a distal direction to engage with the capsule 42 and has returned with the capsule 42 to complete a full outward and return stroke.

When the actuator 206 reaches the fully activated position R, the drive wheel 216 disengages with the engagement surface 218 of the rack 210. The torsion spring TS1 creates a return force that biases the actuator 206 back to the neutral position P, and the torsion spring TS2 provides a return force that returns the drive wheel 212 back to its initial position. In other words, when the transfer gear 216 is disengaged with the engagement surface 218, the torsion springs TS1 and TS2 recover their energy and return the actuator 206 and the rod 60, respectively, back to their initial positions.

A suture system is disclosed having an actuator mechanism that provides bi-directional suturing needle movement derived from a simple uni-directional movement of the actuator. The actuator is configured to provide out-and-in needle movement that cooperates to engage with a capsule attached to a suture to throw a stitch through tissue. The uni-directional movement of the actuator ensures the surgeon that a complete cycle of needle movement is achieved with one squeeze of the actuator.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A suturing assembly configured to place suture in tissue, the suturing assembly comprising:

a handle comprising a brace and an actuator attached to the handle, the actuator having a neutral position that is distal the brace;

a shaft coupled to the handle and defining a longitudinal axis of the assembly; and a head coupled to the shaft, the head comprising a proximal portion housing a needle movable through a needle exit port of the head and a distal end spaced apart from the proximal portion by a throat, the needle connected with the actuator by a rod that extends through the shaft, the distal end of the head radially offset from the longitudinal axis and defining a cavity;

wherein, as the actuator is displaced from the neutral position to the brace, the needle moves both in a first direction out of the needle exit port into the cavity formed in the distal end of the head and in a second direction out of the cavity formed in the distal end of the head and into the needle exit port.

2. The suturing assembly of claim 1, wherein the movement of the actuator from the neutral position to the brace moves the needle away from the longitudinal axis.

3. The suturing assembly of claim 1, wherein a transfer gear is engaged between an engagement surface of the actuator and a drive wheel that is connected with the rod.

4. The suturing assembly of claim 3, wherein the engagement surface is biased by a spring to allow the engagement surface to decouple from the transfer gear.

5. The suturing assembly of claim 1, further comprising:
a capsule attached to a length of suture, the capsule sized for placement in the cavity formed in the distal end of the head.

6. The suturing assembly of claim 5, wherein movement of the needle in the first direction creates a channel in tissue and movement of the needle in the second direction pulls the capsule and the length of suture through the channel in the tissue to suture tissue.

7. The suturing assembly of claim 1, wherein the actuator comprises a trigger coupled to a rod disposed in the shaft, the rod extending between the handle and the needle.

8. The suturing assembly of claim 1, wherein the shaft comprises a rigid shaft.

* * * * *